US008563265B2

(12) United States Patent
Mayer et al.

(10) Patent No.: US 8,563,265 B2
(45) Date of Patent: Oct. 22, 2013

(54) ANALYTICAL INSTRUMENT AND METHOD FOR EVALUATING MICROBIAL CONTAMINATION OF AN OBJECT

(75) Inventors: Daniel W. Mayer, Wyoming, MN (US); Robert Lee Demorest, Maple Grove, MN (US)

(73) Assignee: Mocon, Inc., Minneapolis, MN (US)

( * ) Notice: Subject to any disclaimer, the term of this patent is extended or adjusted under 35 U.S.C. 154(b) by 0 days.

(21) Appl. No.: 13/450,025

(22) Filed: Apr. 18, 2012

(65) Prior Publication Data

US 2012/0270261 A1   Oct. 25, 2012

Related U.S. Application Data

(60) Provisional application No. 61/477,695, filed on Apr. 21, 2011.

(51) Int. Cl.
*C12Q 1/06* (2006.01)

(52) U.S. Cl.
USPC .......................................................... 435/39

(58) Field of Classification Search
USPC .......................................................... 435/39
See application file for complete search history.

(56) References Cited

U.S. PATENT DOCUMENTS

| 5,403,721 A * | 4/1995 | Ward et al. ...................... 435/34 |
| 7,100,461 B2 | 9/2006 | Bradley et al. |
| 7,115,385 B2 | 10/2006 | Breitschwerdt et al. |
| 7,238,496 B2 * | 7/2007 | Li et al. ............................ 435/34 |
| 2008/0057535 A1 * | 3/2008 | Akamatsu et al. ............. 435/39 |
| 2011/0117025 A1 | 5/2011 | Dacosta et al. |
| 2011/0207115 A1 | 8/2011 | Smith et al. |
| 2011/0256584 A1 | 10/2011 | Matoulkova et al. |

FOREIGN PATENT DOCUMENTS

| EP | 0105747 A1 | 4/1984 |
| EP | 0927353 B1 | 5/2007 |

OTHER PUBLICATIONS

Luxcel Biosciences Ltd., GreenLight™: Same-Day Analysis of Aerobic Plate Counts (APCs,TVCs) in raw meat samples, Rev. Jul. 2010, available online at: luxcel.com/wp-content/uploads/2012/07/Greenlight-App-Note1.pdf.*
Strianese et al., A protein-based oxygen biosensor for high-throughput monitoring of cell growth and cell viability, Analytical Biochemistry 385 (2009) 242-248.*
Traynor et al., Development and Testing of a Rapid Protocol for Environmental Swabs Using an Oxygen-Depletion Technology, Accessed Jan. 8, 2013, online at: www.mocon.com/pdffoodsafety/AIFP%20Reprint%20(2).pdf.*

(Continued)

*Primary Examiner* — Karen Cochrane Carlson
*Assistant Examiner* — Jennifer M Tichy
(74) *Attorney, Agent, or Firm* — Sherrill Law Offices, PLLC

(57) ABSTRACT

An instrument and method for ascertaining a viable aerobic microbe count at $t_o$ employing a two-point calibration curve of $t_{threshold}$ to TVC for each type of sample. One point on the calibration curve is the x-intercept value (i.e., an estimated or experimental value for the logarithm of the minimum viable aerobic microbe count at commencement of testing ($t_o$) in a sample effective for causing the sample to reach $t_{Threshold}$ substantially instantaneously upon commencement of incubation). The other point is ascertained experimentally from a sample having a smaller known viable aerobic microbe count at $t_o$.

17 Claims, 2 Drawing Sheets

(56) References Cited

OTHER PUBLICATIONS

O'Mahony, Fiach et al., "Rapid High-Throughput Assessment of Aerobic Bacteria in Complex Samples by Fluorescence-Based Oxygen Respirometry", Applied and Environmental Microbiology, American Society for Microbiology, Feb. 2006, p. 1279-1287 vol. 72, No. 2.

O'Mahony, Fiach et al., "Analysis of total aerobic viable counts in samples of raw meat using fluorescence-based probe and oxygen consumption assay", www.elsevier.com/locate/foodcont, 2008.

* cited by examiner

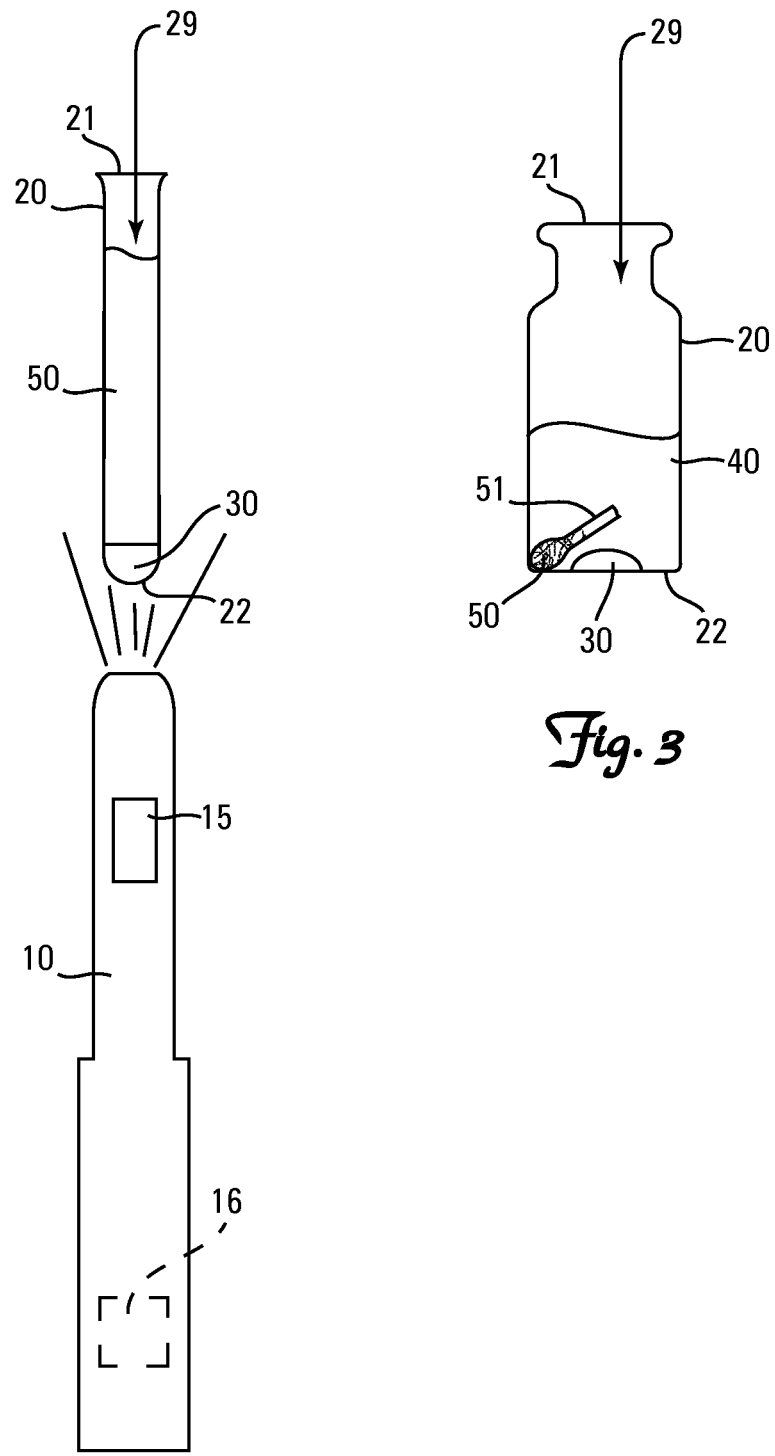

ANALYTICAL INSTRUMENT AND METHOD FOR EVALUATING MICROBIAL CONTAMINATION OF AN OBJECT

This application claims the benefit of U.S. Provisional Application No. 61/477,695, filed Apr. 21, 2011.

BACKGROUND

The Total Viable Count (TVC) of aerobic bacteria in a sample can be determined by monitoring depletion of oxygen in the sample over time until a threshold value is reached based upon a previously established calibration curve of tthreshold to TVC. See, for example, F. C. O'Mahony and D. B. Papkovsky, Rapid High-Throughput Assessment of Aerobic Bacteria in Complex Samples by Fluorescence-Based Oxygen Respirometry, Applied and Environmental Microbiology, vol. 72, No. 2, February 2006, pp. 1279-1287.

The calibration curves of $t_{threshold}$ to TVC are established by experimentally determining $t_{threshold}$ for several samples containing known different starting TVCs, plotting the results in semilogarithmic scale and establishing a linear equation for the regression line.

While such systems are relatively quick, easy and accurate, the time and expense involved in establishing a calibration curve of $t_{threshold}$ to TVC for each type of sample (e.g., each SKU or each type of swab or swab-sampling protocol) renders the system unsuitable for commercial use, particularly for companies with an ever changing product line and/or with dozens or even thousands of different SKUs.

Accordingly, a substantial need exists for a system and method of quickly and inexpensively obtaining an accurate calibration curve of $t_{threshold}$ to TVC for each type of sample.

SUMMARY OF THE INVENTION

I have surprisingly discovered that an accurate calibration curve of $t_{threshold}$ to TVC for each type of sample can be established from just two-points, wherein one point is the x-intercept value (i.e., an estimated or experimental value for the logarithm of the minimum viable aerobic microbe count at commencement of testing ($t_o$) in a sample effective for causing the sample to reach $t_{Threshold}$ substantially instantaneously upon commencement of incubation), and the other point is ascertained experimentally from a sample having a smaller known viable aerobic microbe count at $t_o$, preferably a viable aerobic microbe count at $t_o$ which is several orders of magnitude smaller than $t_o$ at the x-intercept.

A first aspect of the invention is a method for evaluating microbial contamination of an object, comprising the steps of: (a) incubating a sample taken from the object starting at time $t_o$, (b) periodically ascertaining an $O_2$ concentration of the incubating sample until the detected $O_2$ concentration decreases below a threshold value, (c) establishing the time period $t_{Threshold}$ measured from $t_o$ to the time at which the $O_2$ concentration decreased below the threshold value, and (d) correlating $t_{Threshold}$ to a viable aerobic microbe count in the sample prior to incubation, utilizing the linear equation:

$$y = mx + b \quad \text{(Eq. 1)}$$

wherein:
x=logarithm of the viable aerobic microbe count per unit weight of, volume of or area swabbed to obtain a sample at $t_o$
$y = t_{Threshold}$
x-intercept=$(-b/m)$=an estimated or experimental value for the logarithm of the minimum viable aerobic microbe count at $t_o$ in a sample effective for causing the sample to reach $t_{Threshold}$ substantially instantaneously upon commencement of incubation, and $m(\text{slope}) = (y_2 - y_1)/(x_2 - x_1)$ wherein:

$x_1$ and $y_1$ are ascertained experimentally by establishing $t_{Threshold}$ for a sample taken from an object having a known x, and $x_2$ and $y_2$ are values of x and y at the x-intercept $(-b/m, 0)$.

The sample is preferably incubated in a hermetically sealed chamber in the presence of an oxygen sensitive photoluminescent dye with $O_2$ concentration of the incubating sample ascertained by measuring fluorescence of the oxygen sensitive dye.

A second aspect of the invention is an analytical instrument comprising an $O_2$ sensor and a microprocessor in electrical communication with the sensor, wherein the instrument is effective for (i) periodically ascertaining an $O_2$ concentration of an incubating sample taken from an object, (ii) determining a time period $t_{Threshold}$ from a time $t_o$ at which incubation of the sample commenced to a time at which an ascertained $O_2$ concentration for the sample first falls below a threshold value, (iii) correlating $t_{Threshold}$ to a viable aerobic microbe count in the sample prior to incubation, utilizing the linear equation:

$$y = mx + b \quad \text{(Eq. 1)}$$

wherein:
x=logarithm of the viable aerobic microbe count per unit weight of, volume of or area swabbed to obtain a sample at $t_o$
$y = t_{Threshold}$
x-intercept=$(-b/m)$=an estimated or experimental value for the logarithm of the minimum viable aerobic microbe count at $t_o$ in a sample effective for causing the sample to reach $t_{Threshold}$ substantially instantaneously upon commencement of incubation, and $m(\text{slope}) = (y_2 - y_1)/(x_2 - x_1)$ wherein:

$x_1$ and $y_1$ are ascertained experimentally by establishing $t_{Threshold}$ for a sample taken from an object having a known x, and $x_2$ and $y_2$ are values of x and y at the x-intercept $(-b/m, 0)$ and (iv) transmitting a correlated value of x to a peripheral device.

The $O_2$ sensor preferably comprises an oxygen sensitive photoluminescent dye having a luminescent lifetime and a reader effective for determining $O_2$ concentration in an environment in fluid communication with the dye by measuring fluorescence of the oxygen sensitive dye.

BRIEF DESCRIPTION OF THE DRAWINGS

FIG. 2 is an exemplary $O_2$ sensor and microprocessor taking a reading from an incubating sample in accordance with the present invention wherein the sample is a liquefied specimen detached from the object being evaluated.

FIG. 3 is an exemplary incubating sample in accordance with the present invention wherein the sample is a swab-sampling taken from the surface of an object being evaluated.

DETAILED DESCRIPTION OF A PREFERRED EMBODIMENT

Nomenclature

Figure 1:
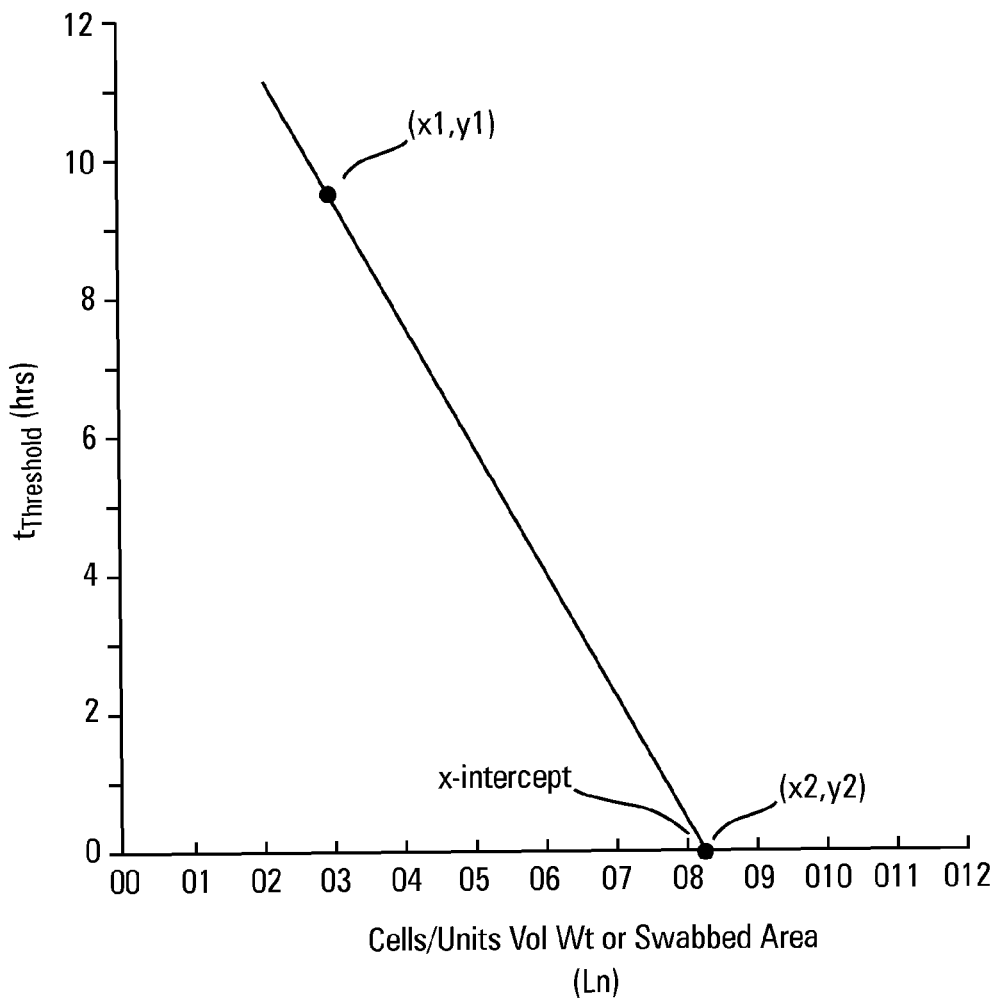
FIG. 1 is an exemplary calibration curve prepared in accordance with the present invention.

10 Interrogation Device
15 Display Component of Interrogation Device
16 Microprocessor
20 Vessel, Vial or Cuvette
21 Open Top End of Vessel, Vial or Cuvette
22 Closed Bottom End of Vessel, Vial or Cuvette
29 Retention Chamber of Vessel, Vial or Cuvette
30 Probe
40 Growth Media
50 Sample
51 Swab containing Sample Construction The invention is directed to an instrument and method for evaluating microbial contamination of an object (not shown) by monitoring changes in oxygen concentration in an incubating sample 50 taken from the object (not shown) and correlating observed changes to a viable aerobic microbe count in the sample 50 prior to incubation employing a readily calibratable linear equation.

The object (not shown) to be evaluated for microbial contamination is essentially unlimited, ranging from solids such as equipment used in meat processing and packaging facilities, food preparation countertops, medical instruments, fruits, vegetables and meats, and liquids such as dairy products, water retained within a water tower, biological samples, sewage treated by a sewage treatment system, water flowing in rivers and streams, etc.

Persons of routine skill in the art are capable of obtaining and preparing suitable samples 50 from the various objects (not shown) of interest, including specifically but not exclusively detaching a specimen from a solid object (not shown) such as a chicken breast, a swab-sampling taken from a hard surface such as a sanitized stainless steel countertop used in a food preparation area, an aliquot taken from sewage treatment facility, etc.

Each sample 50 is placed within the retention chamber 29 of a vessel 20 having an open top end 21, a closed bottom end 22, and a probe 30 within the retention chamber 29. The vessel 20 is preferably a vial or cuvette having a high aspect ratio of depth to circumference, such as disclosed in United States Patent Application Publication 2009/0029402, which disclosure is incorporated herein by reference. Since a preferred vessel 20 is a vial or cuvette 20, the balance of the disclosure shall reference the vessel 20 as a vial 20 without intending to be limited thereby.

The preferred methods and instruments described herein monitor microbial consumption of oxygen ($O_2$) in a sample 50 based upon the quenching of photoluminescence by oxygen ($O_2$). Luminescence encompasses both fluorescence and phosphorescence. Electromagnetic radiation in the ultraviolet or visible region is used to excite molecules to higher electronic energy levels. The excited molecules lose their excess energy by one of several methods. One of those methods is fluorescence. Fluorescence refers to the radiative transition of electrons from the first excited singlet state to the singlet ground state ($S_1$ to $S_0$). The lifetime of fluorescence is relatively short, approximately $10^{-9}$ to $10^{-7}$ seconds. However, intersystem crossing from the lowest excited singlet state to the triplet state often occurs and is attributed to the crossing of the potential energy curves of the two states. The triplet state so produced may return to the ground state by a radiative process known as phosphorescence. Phosphorescence is the radiative relaxation of an electron from the lowest excited triplet state to the singlet ground state ($T_1$ to $S_0$). Because the transition that leads to phosphorescence involves a change in spin multiplicity, it has a low probability and hence a relatively long lifetime of $10^{-4}$ to 10 seconds. Fluorescent and phosphorescent lifetime is known to change in a defined fashion relative to changes in the partial pressure of an analyte ($P_A$) capable of quenching the photoluminescent molecules. Hence, the $P_A$ in fluid communication with a photoluminescent material can be determined by measuring photoluminescence lifetime.

In a preferred embodiment, the probes 30 are optically-active, oxygen partial pressure sensitive materials configured and arranged to experience changes in oxygen partial pressure $P_{O2}$ in a sample 50 placed within the retention chamber 29 of a vial 20. The oxygen-sensitive material is preferably a photoluminescent dye embedded within an oxygen permeable polymer matrix. Alternatively, the oxygen-sensitive photoluminescent dye can be dissolved in the sample 50 and/or any added growth media 40.

The oxygen-sensitive photoluminescent dye may be selected from any of the well-known oxygen sensitive photoluminescent dyes. One of routine skill in the art is capable of selecting a suitable dye based upon the intended use of the probe. A nonexhaustive list of suitable oxygen sensitive photoluminescent dyes includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium (III) or osmium(II).

Typically, the hydrophobic oxygen-sensitive photoluminescent dye is compounded with a suitable oxygen-permeable and hydrophobic carrier matrix. Again, one of routine skill in the art is capable of selecting a suitable oxygen-permeable hydrophobic carrier matrix based upon the intended use of the probe 30 and the selected dye. A nonexhaustive list of suitable polymers for use as the oxygen-permeable hydrophobic carrier matrix includes specifically, but not exclusively, polystryrene, polycarbonate, polysulfone, polyvinyl chloride and some co-polymers.

When the probe 30 is based on the quenching of photoluminescence by an analyte, the vial 20, or at least that portion of the vial 20 coated with the probe 30, must allow radiation at the excitation and emission wavelengths to be transmitted to and received from the probe 30 with minimal interference.

Instruments 10 for interrogating probes 30 based on the quenching of photoluminescence by an analyte are well known and commercially available from various sources, including Becton Dickinson of Franklin Lakes, N.J. and Mocon, Inc. of Minneapolis, Minn. Such instruments 10 typically include or are equipped to communicate with a microprocessor 16, computer memory (not shown), an input device such as a mouse (not shown) and/or a keyboard (not shown), a display 15 and a printer (not shown).

Manufacture of Probe 30 Containing Vials 20

The probe 30 containing vials 20 can be conveniently manufactured by (A) preparing a coating cocktail (not shown) which contains the photoluminescent oxygen-sensitive dye and the oxygen-permeable polymer in an organic solvent (not shown) such as ethylacetate, (B) depositing the cocktail into the bottom 22 of the retention chamber 29, such as by using a syringe (not shown), and (C) allowing the cocktail (not shown) to dry, whereby a solid-state coating is formed within the retention chamber 29 at the bottom 22 of the vial 20, thereby forming a probe 30 within the vial 20.

Generally, the concentration of the polymer in the organic solvent should be in the range of 0.1 to 20% w/w, with the ratio of dye to polymer in the range of 1:20 to 1:10,000 w/w, preferably 1:50 to 1:5,000 w/w.

Use

Microbial contamination of an object can be evaluated by (a) obtaining and depositing a sample 50 taken from the object into the retention chamber 29 of a vessel 20 equipped with a probe 30, (b) optionally digesting or stomaching the sample 50 for a defined period of time, (c) optionally depositing growth media 40 into the retention chamber 29 when necessary and appropriate for supporting growth of microbes contained within the deposited sample 50, (d) incubating the sample 50 starting at time $t_o$, (e) periodically ascertaining an $O_2$ concentration of the incubating sample 50 until the detected $O_2$ concentration at the probe 30 decreases below a threshold value, (f) establishing the time period $t_{Threshold}$ measured from $t_o$ to the time at which the $O_2$ concentration decreased below the threshold value, and (g) correlating $t_{Threshold}$ to a viable aerobic microbe count in the sample prior to incubation, utilizing the linear equation:

$$y = mx + b \quad \text{(Eq. 1)}$$

wherein:
x = logarithm of the viable aerobic microbe count per unit weight of, volume of or area swabbed to obtain a sample at $t_o$
$y = t_{Threshold}$
x-intercept = $(-b/m)$ = an estimated or experimental value for the logarithm of the minimum viable aerobic microbe count at $t_o$ in a sample effective for causing the sample to reach $t_{Threshold}$ substantially instantaneously upon commencement of incubation, and $$m(\text{slope}) = (y_2 - y_1)/(x_2 - x_1) \text{ wherein:}$$

$x_1$ and $y_1$ are ascertained experimentally by establishing $t_{Threshold}$ for a sample taken from an object having a known x, and $x_2$ and $y_2$ are values of x and y at the x-intercept $(-b/m, 0)$.

The sample is preferably incubated in a hermetically sealed chamber in the presence of an oxygen sensitive photoluminescent dye with $O_2$ concentration of the incubating sample ascertained by measuring fluorescence of the oxygen sensitive dye with an analytical instrument 10 comprising an $O_2$ sensor and a microprocessor in electrical communication with the sensor.

The $O_2$ concentration threshold value may be established as (i) a % decrease in the atmospheric concentration of $O_2$, (ii) a % decrease in the concentration of $O_2$ in fluid communication with the probe 30 in the vessel 20 relative to the $O_2$ concentration in fluid communication with the probe 30 in the vessel 20 at $t_o$, or (iii) an absolute value of the concentration of $O_2$ within the retention chamber 29 of the vessel 20. When either option (i) or option (ii) is employed a preferred % decrease is a decrease of between 25% and 75%. When option (iii) is employed an absolute value of between 5% and 16% is preferred.

When the sample 50 is digested or stomached, $t_o$ should be established after the sample 50 has been stomached for a defined period of time $t_{Stomach}$. This defined period of time is preferably set to occur within the lag phase growth period of bacteria within the sample 50, with a time period of less than 60 minutes typically acceptable, and a time period of less than 5 minutes often desired.

The oxygen concentration within the retention chamber 29 can be checked on substantially any desired scheduled with readings spaced more than two hours apart tending to produce results subject to excessive inaccuracy in the final ascertained value for TVC at $t_o$ while readings spaced less than ½ hour apart require substantial additional time and effort with only modest improvement in accuracy of the final ascertained value for TVC at $t_o$.

The radiation emitted by the excited probe 30 can be measured in terms of intensity and/or lifetime (rate of decay, phase shift or anisotropy), with measurement of lifetime generally preferred as a more accurate and reliable measurement technique when seeking to establish oxygen concentration via measurement of the extent to which the dye has been quenched by oxygen.

The Linear Equation and Calibration Thereof

In order to determine Total Viable Count (TVC) of aerobic bacteria in a sample 50 from the time required for the hermetically sealed sample 50 to consume a defined quantity or % of oxygen requires use of a previously established calibration curve of $t_{threshold}$ to TVC such as depicted in FIG. 1.

Traditionally, such calibration curves of $t_{threshold}$ to TVC are established by experimentally determining $t_{threshold}$ for several samples 50 of the same sample type (e.g., ground water, milk, chicken breast, ground hamburger, ground egg shells, swab sample taken from the exterior of an unbroken egg, swab sample taken from a sanitized stainless steel food processing work surface, etc.) containing known different starting TVCs, plotting the results in semilogarithmic scale and establishing a linear equation for the regression line.

I have surprisingly discovered that an accurate calibration curve of TVC for $t_{threshold}$ to each type of sample can be established from just two-points, wherein one point is the x-intercept value (i.e., an estimated or experimental value for the logarithm of the minimum viable aerobic microbe count at commencement of testing ($t_o$) in a sample 50 effective for causing the sample 50 to reach $t_{Threshold}$ substantially instantaneously upon commencement of incubation), and the other point is ascertained experimentally from a sample 50 having a smaller known viable aerobic microbe count at $t_o$, preferably a viable aerobic microbe count at $t_o$ which is several orders of magnitude smaller than $t_o$ at the x-intercept. The logarithms employed are preferably natural logarithms.

Once a calibration curve of $t_{threshold}$ to TVC has been established for a sample type, a viable aerobic microbe count in a sample 50 of that sample type prior to incubation can be ascertained from an experimentally obtained value for $t_{Threshold}$ measured from $t_o$ to the time at which the $O_2$ concentration decreased below a threshold value utilizing the linear equation:

$$y = mx + b \quad \text{(Eq. 1)}$$

wherein:
x = logarithm of the viable aerobic microbe count per unit weight of, volume of or area swabbed to obtain a sample at $t_o$
$y = t_{Threshold}$
x-intercept = $(-b/m)$ = an estimated or experimental value for the logarithm of the minimum viable aerobic microbe count at $t_o$ in a sample effective for causing the sample to reach $t_{Threshold}$ substantially instantaneously upon commencement of incubation, and $$m(\text{slope}) = (y_2 - y_1)/(x_2 - x_1) \text{ wherein:}$$

$x_1$ and $y_1$ are ascertained experimentally by establishing $t_{Threshold}$ for a sample taken from an object having a known x, and $x_2$ and $y_2$ are values of x and y at the x-intercept (−b/m, 0).

The x-intercept value is preferably established experimentally, but can be estimated. When estimated, an estimated value of between 6 and 10, most often between 7 and 9, has been found to produce acceptable results in most situations.

EXAMPLES

Example 1

Prophetic

Detached Sample

An interrogation device 10 capable of determining $O_2$ concentration in a sample 50 in fluid communication with a probe 30 by measuring fluorescence of the oxygen sensitive dye in the probe 30 is provided with values for m (slope) and b (y-intercept) for various specified types of samples, whereby Equation 1 can be solved for x (logarithm of the viable aerobic microbe count per unit weight of, volume of or area swabbed to obtain a sample at $t_o$) once y ($t_{Threshold}$) is experimentally obtained from a sample 50 of one of the specified types of samples 50.

Samples 50 of a processed food product containing a preservative, matching a type of sample 50 for which the interrogation device 10 has a value for m and b, are taken from a processing line every hour on the half hour to ascertain viable bacterial count (TVC, APC or CFU) just prior to packaging. Each sample 50 is transported from the processing line to a testing room, digested for a predefined period of time, and a known volume or weight of the sample 50 deposited into a barcoded vial 20 containing a photoluminescent oxygen-sensitive probe 30.

An initial reading is taken from the probe 30 in each vial 20 containing a sample 50 by interrogating the probe 30 with an interrogation device 10. The type of sample 50, results of the initial reading, and the time of day at which the initial reading is taken are recorded and correlated to the barcode of the tested vial 20. Upon completion of the initial interrogation a schedule is established for subsequent interrogations of each vial 20 and the vials 20 are placed into an incubation chamber (not shown).

Each vial 20 is subsequently interrogated on the established interrogation schedule. The results of each interrogation and elapsed time since the initial interrogation for each vial 20 are recorded.

Each vial 20 is interrogated until a threshold value is reached in the readings from the probe 30, at which time the interrogation device 10 indicates that testing is complete, determines viable bacterial count (x) employing the previously provided values for m and b for the type of sample 50 tested and the experimentally ascertained value for y, and provides the operator with an indication of whether the sample 50 contained an ACCEPTABLE or UNACCEPTABLE viable bacterial count based upon a preestablished threshold value for x. Upon request, the operator can obtain the actual value of the viable bacterial count from the interrogation device 10.

Example 2

Prophetic

Swabbed Sample

An interrogation device 10 capable of determining $O_2$ concentration in a sample 50 in fluid communication with a probe 30 by measuring fluorescence of the oxygen sensitive dye in the probe 30 is provided with values for m (slope) and b (y-intercept) for various specified types of samples, whereby Equation 1 can be solved for x (logarithm of the viable aerobic microbe count per unit weight of, volume of or area swabbed to obtain a sample at $t_o$) once y ($t_{Threshold}$) is experimentally obtained from a sample 50 of one of the specified types of samples 50.

Samples 50, obtained by swabbing known areas of a work surface in a food processing plant, matching a type of sample 50 for which the interrogation device 10 has a value for m and b, are taken each time the work surface is cleaned and sanitized to ascertain viable bacterial count (TVC, APC or CFU) and thereby verify the effectiveness of the cleaning and sanitization process. The sample-containing portion of the swabs 51 are immediately deposited into a barcoded vial 20 containing a photoluminescent oxygen-sensitive probe 30 and a suitable growth medium 40 added.

An initial reading is taken from the probe 30 in each vial 20 containing a sample 50 by interrogating the probe 30 with an interrogation device 10. The type of sample 50, results of the initial reading, and the time of day at which the initial reading is taken are recorded and correlated to the barcode of the tested vial 20. Upon completion of the initial interrogation a schedule is established for subsequent interrogations of each vial 20 and the vials 20 are placed into an incubation chamber (not shown).

Each vial 20 is subsequently interrogated on the established interrogation schedule. The results of each interrogation and elapsed time since the initial interrogation for each vial 20 are recorded.

Each vial 20 is interrogated until a threshold value is reached in the readings from the probe 30, at which time the interrogation device 10 indicates that testing is complete, determines viable bacterial count (x) employing the previously provided values for m and b for the type of sample 50 tested and the experimentally ascertained value for y, and provides the operator with an indication of whether the sample 50 contained an ACCEPTABLE or UNACCEPTABLE viable bacterial count based upon a preestablished threshold value for x. Upon request, the operator can obtain the actual value of the viable bacterial count from the interrogation device 10.

We claim:

1. A method for evaluating microbial contamination of an object, comprising the steps of: (a) incubating a sample taken from the object starting at time $t_o$, (b) periodically ascertaining an $O_2$ concentration of the incubating sample until the detected $O_2$ concentration decreases below a threshold value, (c) establishing the time period $t_{Threshold}$ measured from $t_o$ to the time at which the $O_2$ concentration decreased below the threshold value, and (d) correlating $t_{Threshold}$ to a viable aerobic microbe count in the sample prior to incubation, utilizing the linear equation:

$$y = mx + b \qquad (\text{Eq. 1})$$

wherein:
x = logarithm of the viable aerobic microbe count per unit weight of, volume of or area swabbed to obtain a sample at $t_o$
y = $t_{Threshold}$
x-intercept = (−b/m) = an estimated or experimental value for the logarithm of the minimum viable aerobic microbe count at $t_o$ in a sample effective for causing the sample to reach $t_{Threshold}$ substantially instantaneously upon commencement of incubation, and $m(\text{slope}) = (y_2 - y_1)/(x_2 - x_1)$ wherein:

$x_1$ and $y_1$ are ascertained experimentally by establishing $t_{Threshold}$ for a sample taken from an object having a known x, and $x_2$ and $y_2$ are values of x and y at the x-intercept (−b/m, 0).

2. The method of claim 1 wherein the logarithms are natural logarithms.

3. The method of claim 1 wherein the sample is a specimen detached from the object and x=logarithm of the viable aerobic microbe count per unit weight or volume of a sample at $t_o$.

4. The method of claim 1 wherein the sample is a swab-sampling taken from the surface of the object and x=logarithm of the viable aerobic microbe count per unit area of the object swabbed to obtain a sample at $t_o$.

5. The method of claim 4 wherein the swab-sampling is taken after the surface has been sanitized for purposes of validating sanitization of the surface.

6. The method of claim 3 wherein the object is a foodstuff and $t_o$ occurs after the sample has been stomached for a defined period of time $t_{Stomach}$.

7. The method of claim 6 wherein $t_{Stomach}$ is completed within a lag phase growth of the bacteria.

8. The method of claim 1 wherein an $O_2$ concentration of the incubating sample is ascertained at least once every hour.

9. The method of claim 1 wherein the $O_2$ concentration threshold value is a decrease of between 25% and 75% of the $O_2$ concentration at $t_o$.

10. The method of claim 1 wherein correlating $t_{Threshold}$ to a viable aerobic microbe count in the sample prior to incubation is accomplished by solving the linear equation for x.

11. The method of claim 1 wherein correlating $t_{Threshold}$ to a viable aerobic microbe count in the sample prior to incubation is accomplished by use of a look-up table.

12. The method of claim 1 wherein the x-intercept is an experimental value.

13. The method of claim 1 wherein the x-intercept is an estimated value between 6 and 10.

14. The method of claim 1 wherein the sample is incubated in a hermetically sealed chamber in the presence of an oxygen sensitive photoluminescent dye and $O_2$ concentration of the incubating sample is ascertained by measuring fluorescence of the oxygen sensitive dye.

15. The method of claim 14 wherein luminescent lifetime of the oxygen sensitive dye changes in response to changes in the $O_2$ concentration of the incubating sample.

16. The method of claim 14 wherein the oxygen-sensitive photoluminescent dye is embedded within an oxygen-permeable hydrophobic polymer matrix in physical contact with the sample.

17. The method of claim 14 wherein the oxygen-sensitive photoluminescent dye is dissolved in the sample.

* * * * *